United States Patent
Dirauf et al.

(10) Patent No.: US 9,554,953 B2
(45) Date of Patent: Jan. 31, 2017

(54) MOBILE MEDICAL DEVICE AND METHOD FOR CONTROLLING A MOVEMENT OF THE MOBILE MEDICAL DEVICE

(71) Applicants: Franz Dirauf, Ebensfeld (DE); Dieter Heinl, Erbendorf (DE); Peter Klemm, Hanau (DE); Michael Koerth, Fürth (DE)

(72) Inventors: Franz Dirauf, Ebensfeld (DE); Dieter Heinl, Erbendorf (DE); Peter Klemm, Hanau (DE); Michael Koerth, Fürth (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/609,877

(22) Filed: Jan. 30, 2015

(65) Prior Publication Data

US 2015/0216746 A1    Aug. 6, 2015

(30) Foreign Application Priority Data

Feb. 5, 2014    (DE) .................. 10 2014 202 033

(51) Int. Cl.
*G01C 22/00*    (2006.01)
*A61G 1/02*    (2006.01)
(Continued)

(52) U.S. Cl.
CPC ............... *A61G 1/0275* (2013.01); *A61G 1/04* (2013.01); *A61G 7/012* (2013.01); *A61G 7/018* (2013.01);
(Continued)

(58) Field of Classification Search
CPC ........ A61G 1/0275; A61G 1/04; A61G 7/012; A61G 7/018; A61G 7/08; B62D 1/02; B62D 1/22; B62D 1/283; B62D 15/00; G05D 1/021; G05D 1/0234
See application file for complete search history.

(56) References Cited

U.S. PATENT DOCUMENTS 3,876,255 A    4/1975    Ilon
5,779,637 A *  7/1998    Palkovich .......... G01R 33/3806
                                              324/318
(Continued)

FOREIGN PATENT DOCUMENTS

DE    2354404 A1    5/1974
DE    29518502 U1   12/1996
(Continued)

OTHER PUBLICATIONS

German Office Action for related German Application No. 10 2014 202 033.6, mailed Sep. 2, 2014, with English Translation.

*Primary Examiner* — Ian Jen
(74) *Attorney, Agent, or Firm* — Lempia Summerfield Katz LLC

(57) ABSTRACT

The embodiments relate to a medical device and to a method for controlling a movement of the mobile medical device. The medical device includes a chassis and a control apparatus, wherein the medical device is embodied by the chassis to perform a movement in at least two spatial directions on a plane of motion and to execute a rotary movement about an axis of rotation standing perpendicularly on the plane of motion, and the control apparatus is embodied for controlling the chassis.

15 Claims, 9 Drawing Sheets

(51) Int. Cl.
*A61G 1/04* (2006.01)
*A61G 7/012* (2006.01)
*A61G 7/08* (2006.01)
*G05D 1/02* (2006.01)
*A61G 7/018* (2006.01)
*B62D 1/02* (2006.01)
*B62D 1/22* (2006.01)
*B62D 1/28* (2006.01)
*B62D 15/00* (2006.01)
*A61B 17/00* (2006.01)

(52) U.S. Cl.
CPC . *A61G 7/08* (2013.01); *B62D 1/02* (2013.01); *B62D 1/22* (2013.01); *B62D 1/283* (2013.01); *B62D 15/00* (2013.01); *G05D 1/021* (2013.01); *G05D 1/0234* (2013.01); *A61B 34/30* (2016.02); *A61B 2017/00075* (2013.01); *A61G 2203/14* (2013.01); *A61G 2203/22* (2013.01); *A61G 2203/72* (2013.01); *G05D 2201/0206* (2013.01)

(56) References Cited

U.S. PATENT DOCUMENTS

| | | | | |
|---|---|---|---|---|
| 8,381,331 B2* | 2/2013 | Sharps | ............... | A61G 7/001 5/607 |
| 8,590,074 B2* | 11/2013 | Hornbach | ............... | A61G 7/00 5/600 |
| 8,707,476 B2* | 4/2014 | Sharps | ............... | A61G 13/02 5/607 |
| D720,076 S * | 12/2014 | Sharps | ............... | D24/183 |
| D745,971 S * | 12/2015 | Sharps | ............... | D24/183 |
| 2005/0065675 A1 | 3/2005 | Georgi et al. | | |
| 2007/0174966 A1* | 8/2007 | Lopez-Sansalvador | ............... | A61G 1/0293 5/607 |
| 2008/0202837 A1 | 8/2008 | Macedo Ribeiro et al. | | |
| 2010/0024128 A1* | 2/2010 | Skripps | ............... | A61G 13/04 5/621 |
| 2011/0214588 A1 | 9/2011 | Grubling et al. | | |
| 2011/0238217 A1 | 9/2011 | Kume et al. | | |
| 2012/0023671 A1* | 2/2012 | Miyano | ............... | A61B 6/0407 5/601 |
| 2014/0094997 A1* | 4/2014 | Hyde | ............... | G05D 1/0011 701/2 |
| 2015/0335508 A1* | 11/2015 | Liu | ............... | A61G 7/012 5/611 |

FOREIGN PATENT DOCUMENTS

| | | |
|---|---|---|
| DE | 10336303 A1 | 3/2005 |
| DE | 112006002551 T5 | 9/2008 |
| DE | 102010008014 A1 | 8/2011 |
| DE | 102011006359 A1 | 10/2012 |
| DE | 102012213202 A1 | 1/2014 |
| WO | WO2005041837 A2 | 5/2005 |
| WO | WO2012130930 A1 | 10/2012 |
| WO | WO2014052147 A2 | 4/2014 |

* cited by examiner

MOBILE MEDICAL DEVICE AND METHOD FOR CONTROLLING A MOVEMENT OF THE MOBILE MEDICAL DEVICE

CROSS-REFERENCE TO RELATED APPLICATIONS

This application claims the benefit of DE 10 2014 202 033.6, filed on Feb. 5, 2014, which is hereby incorporated by reference in its entirety.

TECHNICAL FIELD

The embodiments relate to a medical device and to a method for controlling a movement of the mobile medical device.

BACKGROUND

In the medical environment, mobile medical devices are also being deployed to an increasing extent in addition to stationary devices. The mobile medical devices may be embodied as movable and/or drivable. Such mobile medical devices may be deployed at different locations as and when needed or, when not being used, may be removed temporarily from their working environment and parked at a suitable location.

Mobile patient support apparatuses are used, for example, for moving and transferring patients in a hospital-like environment, possibly in order for the patients to undergo an examination by a medical imaging device. The patient couches of the medical imaging devices themselves may be embodied as mobile, as a result of which it is possible to simplify the workflow. Furthermore, medical imaging devices may be embodied as mobile, in which case in particular the gantry of the medical imaging device is embodied as mobile. Mobile X-ray systems, mobile diagnostic stations, mobile devices for intensive medicine, or mobile robot systems for medical applications are also known.

SUMMARY AND DESCRIPTION

The scope of the present invention is defined solely by the appended claims and is not affected to any degree by the statements within this summary. The present embodiments may obviate one or more of the drawbacks or limitations in the related art.

The embodiments relate to a medical device including a chassis and a control apparatus, wherein (1) the medical device is embodied by the chassis to perform a movement in at least two spatial directions on a plane of motion and to execute a rotary movement about an axis of rotation standing perpendicularly on the plane of motion, and (2) the control apparatus is embodied for controlling the chassis.

The chassis may include at least one driving device, for example at least one maximally free-moving roller and/or at least one wheel. The movement of the medical device may be controlled by an operator, wherein the chassis may be embodied as motor-assisted. The chassis is advantageously embodied as an omnidirectional chassis. That is to say that the chassis may enable a movement of the medical device in any desired direction on the plane of motion. There is in particular no need to rotate the medical device in order to effect a change in direction in the movement of the medical device. The change in direction of the medical device may therefore be accomplished directly. The chassis, in particular, the driving device of the chassis, is therefore able to change its orientation on the plane of motion in any desired direction. It is advantageous that the position of the axis of rotation with respect to the medical device may be specified arbitrarily. In this case, the axis of rotation may move in synchronism with the medical device. The axis of rotation may maintain its position with respect to the medical device without any external intervention. The plane of motion is predefined, in particular, on the basis of the floor on which the medical device is moved.

The control apparatus is coordinated with the chassis, in particular, in such a way that it enables the chassis, (e.g., the omnidirectional chassis), to be controlled. For this purpose, the control apparatus may simultaneously actuate at least two, (e.g., all), rollers of the chassis, for example, in order to effect a rotation of the medical device on the plane of motion. Accordingly, the control apparatus is advantageously coordinated with the chassis in such a way that the control apparatus enables the medical device to move particularly easily in at least two spatial directions on the plane of motion and/or allows a rotary movement of the medical device about the axis of rotation. The control apparatus may be embodied as automatic and accordingly enable an automatic control of the chassis. The control apparatus may also be embodied as manual, in which case it is possible, in particular, for an operator to take control of the chassis by the control apparatus. The control apparatus is advantageously embodied simultaneously as automatic and manual, such that a manual control of the chassis by the control apparatus is superposed on an automatic control of the chassis. The control apparatus is embodied, in particular, to send control signals to the chassis, possibly to a motor driving the chassis. Furthermore, the control apparatus is advantageously embodied to receive control signals from an operator, in particular, via an interface.

The proposed chassis for the medical device, in combination with the control apparatus coordinated with the chassis, enables an advantageous movement of the medical device. In particular, the chassis enables the medical device to move particularly easily in several spatial directions on the plane of motion and allows a rotary movement of the medical device about the axis of rotation. The medical device may therefore be maneuvered particularly easily, in particular, even in confined spaces. The medical device may also perform particularly versatile movements on the plane of motion and, for example, travel quickly with the desired orientation to a destination position. The control apparatus may enable an intuitive control of the chassis. In this way, an increase in the efficiency of the workflows in a hospital may be achieved, since mobile medical devices may be moved more quickly to their respective deployment sites.

One embodiment variant provides that the chassis includes at least two omnidirectional wheels. The chassis advantageously includes four omnidirectional wheels. Omnidirectional wheels may have satellite rollers, in particular, in different orientations and/or arrangements. The satellite rollers may be embodied as ball casters. Around their circumference, omnidirectional wheels may have a plurality of rotatable rollers, which are arranged at an angle, (e.g., 45 degrees), to the axis of the omnidirectional wheel. In that case, the at least two omnidirectional wheels may be arranged on opposite sides of the medical device. The oppositely positioned omnidirectional wheels are advantageously arranged axially adjacent to one another, in particular, on an axis line. The oppositely positioned omnidirectional wheels advantageously have an opposite orientation of the roller angles. At a synchronous rotational speed, the opposite omnidirectional wheels accordingly travel forward or backward like conventional wheels, in particular, at right angles to the axis line. If the opposite omnidirectional wheels travel at a different rotational speed, the chassis travels oriented to the left or right in the direction of the axis line, depending on the embodiment of the differential rotational speed. Accordingly, omnidirectional wheels, in particular, two pairs each having two oppositely positioned omnidirectional wheels, form an advantageous omnidirectional chassis for a medical device. By adjusting the rotational speed control of the omnidirectional wheels, in particular, by the control apparatus, the chassis may travel in any desired direction on the plane of motion and/or change its orientation in any desired direction on the plane of motion. The use of omnidirectional wheels also enables a particularly easy rotary movement of the medical device about the axis of rotation. In this case, the omnidirectional wheels may be driven electrically, wherein the control apparatus is able to send signals to the electric drives of the omnidirectional wheels in order to change the rotational speed of the omnidirectional wheels and in that way to change the direction of travel of the medical device. The omnidirectional wheels described are, in particular, also called Mecanum wheels. It goes without saying that other omnidirectional wheels deemed suitable by the person skilled in the art may also be employed.

One embodiment variant provides that the control apparatus includes at least one control element that is embodied for controlling the chassis and to be operated by an operator. The control apparatus may be embodied together with the control element in such a way that a movement of the control element in one direction by the operator leads to a movement of the chassis in the direction of movement of the control element. For this purpose, in particular, the movement of the control element is detected and processed by the control apparatus, the control apparatus controlling the chassis on the basis of the detected and processed movement of the control element. Accordingly, the control element may be embodied for example as a joystick and/or control lever, the joystick allowing a deflection in at least two spatial directions. The deflection of the joystick may lead to a movement of the chassis in the corresponding spatial direction on the plane of motion. Alternatively or in addition, the control element may also be embodied as a twist grip or another control element deemed suitable by the person skilled in the art. Accordingly, the movement of the control element advantageously has at least two degrees of freedom that are coordinated with the at least two spatial directions of the movement of the medical device. If an omnidirectional chassis is employed for moving the medical device, the control element will advantageously be likewise movable in any spatial directions parallel to the plane of motion. Accordingly, the control element advantageously supports an intuitive and interactive control of the chassis. The control apparatus may also have a plurality of control elements, in particular, arranged at different positions of the medical device. For example, a control element may be mounted at each of two opposite sides of the medical device.

One embodiment variant provides that the at least one control element has a longitudinal axis and is embodied to perform a control element rotary movement about the longitudinal axis of the at least one control element. In such an embodiment, the control apparatus is embodied to initiate a rotary movement of the medical device about the axis of rotation on the basis of the control element rotary movement. Accordingly, a rotary movement of the medical device, (e.g., of the chassis of the medical device), may be triggered by a control element rotary movement, a rotation of the control element. Advantageously, the axis of rotation may in this case be set and/or varied, (for example, as described in the following paragraph), by the operator or automatically. The rotary movement of the medical device about the axis of rotation is advantageously executed around the currently selected axis of rotation. The translation of the control element rotary movement into a rotary movement of the chassis enables the operator to control the medical device in a particularly intuitive and simple manner. The medical device is also able to negotiate corners, whereby a linear movement of the control element is overlaid with a control element rotary movement. Alternatively, it is also possible to activate an operating mode in which a linear movement of the control element that deviates in particular from the current direction of travel of the medical device is interpreted as a tangential movement about the axis of rotation and initiates a rotation of the chassis about the axis of rotation.

One embodiment variant provides that the at least one control element is embodied to perform a vertical control element movement perpendicularly to the plane of motion, the control apparatus being embodied to initiate a displacement of the axis of rotation of the medical device on the basis of the vertical control element movement of the at least one control element. In this case, the vertical control element movement may be effected along the longitudinal axis of the control element. Accordingly, the axis of rotation may be set and/or varied particularly intuitively by the operator. Furthermore, the possible degrees of freedom of the control element are optimally exploited. In this case, the axis of rotation may be displaced on the plane of motion. The axis of rotation may be displaced in relation to the medical device. The axis of rotation may therefore be advantageously configured to suit a cornering situation.

One embodiment variant provides that the at least one control element includes a contactless control element. For example, the contactless control element may detect a movement of the operator, (e.g., a gesture and/or a hand movement). The contactless control element may process the detected movement, whereupon the control apparatus controls the chassis on the basis of the detected movement. For example, a hand movement of the operator to the left may effect a leftward movement of the mobile medical device. For this purpose, the contactless control element may include a camera that is mounted on the mobile medical device. The camera may be embodied to acquire two-dimensional and/or three-dimensional images. The contactless control element accordingly enables a particularly intuitive control of the, in particular, omnidirectional, chassis of the medical device.

One embodiment variant provides that the at least one control element includes a force sensor, the control apparatus controlling the chassis on the basis of a force acting on the at least one control element and measured by the force sensor. For that purpose, the force sensor is embodied to measure the external force acting on the control element. Accordingly, the force sensor may be advantageously positioned, (e.g., on the control element or inside the control element), for the purpose of detecting the force. In this case, the force is exerted in particular by the operator, in particular, when the medical device is being moved by the control element. The force may be, for example, a push or pull exerted on the control element by the operator. Alternatively or in addition, the at least one control element may also include a torque sensor, the control apparatus being embodied to detect a torque acting on the at least one control element and measured by the torque sensor. The control apparatus controls a rotary movement of the chassis on the basis of the detected torque. The control element may also include further sensors deemed suitable by the person skilled in the art. The control apparatus may control the chassis on the basis of an equation of motion including an, in particular, virtual, mass and/or friction of the object that is to be moved. The control apparatus may additionally take into account the direction of the detected force and/or of the measured torque. Accordingly, the forces and/or torques exerted on the control element by the operator may be detected directly, the control apparatus being able to control the corresponding travel movement of the medical device on the basis of the detected forces and/or torques. Accordingly, a particularly intuitive control of the movement of the medical device is made possible for the operator. Forces exerted on the control element in a jerky manner by the operator may advantageously be smoothed such that the medical device executes a jerk-free movement.

One embodiment variant provides that the medical device includes a sensor unit having at least one sensor, the control apparatus controlling the chassis on the basis of signals detected by the at least one sensor of the sensor unit. In particular, the control apparatus controls the chassis automatically on the basis of the detected signals. The sensor unit may include one or more sensors. An individual sensor of the sensor unit may be embodied as a two-dimensional optical sensor, three-dimensional optical sensor, laser measurement sensor, acoustic sensor, magnetic field sensor, electric field sensor, induction sensor, radio wave sensor, or as another sensor deemed suitable by the person skilled in the art. The sensor unit may include a plurality of different individual sensors, in particular, in any combination whatsoever. In this case, the control of the movement of the medical device on the basis of the detected signals may be used particularly advantageously in combination with the chassis, (e.g., omnidirectional chassis). The particularly simple change in direction and/or change in alignment of the medical device afford the medical device a particularly advantageous possibility for following the movement path specified by the detected signals.

One embodiment variant provides that the sensor unit includes at least one environmental sensor that is embodied to detect signals from a spatial environment of the medical device. A movement of the medical device may be controlled by the control apparatus on the basis of the information about the environment of the medical device acquired by the environmental sensor. The environmental sensor is embodied in particular as an optical sensor. The environmental sensor is advantageously embodied to sample the spatial environment of the medical device. Accordingly, the environmental sensor is able to survey the environment of the medical device.

One embodiment variant provides that the sensor unit includes at least one obstacle sensor that is embodied to detect signals from obstacles in respect of the movement of the medical device. The obstacle sensor may be embodied as a contactless, (e.g., optical), or as a tactile sensor. Obstacles in respect of the movement of the medical device are located, in particular, in the specified movement path of the medical device. In this context, obstacles may be, for example, objects or persons. On the basis of the signals of the obstacle sensor, (for example, if the obstacle sensor detects an obstacle in the movement path of the medical device), the control apparatus may stop or slow down the chassis of the medical device or adjust the movement of the medical device so that the medical device skirts around the obstacle. The control apparatus may also cause the medical device to follow a moving obstacle along the specified path, in which eventuality the speed of the medical device may be adjusted automatically to the speed of the moving obstacle. Accordingly, the obstacle sensor enables an increased level of safety in respect of the movement of the medical device.

One embodiment variant provides that the control apparatus has a destination specification unit that enables an operator to choose a destination for the medical device, the control apparatus moving the medical device to the chosen destination by the chassis. The movement of the medical device to the chosen destination may be effected on the basis of the signals of the sensors of the sensor unit of the medical device. The destination specification unit may also allow the operator to choose a desired arrival time of the medical device. Accordingly, the medical device may, for example, arrive punctually for a planned medical examination at the correct location.

The embodiments furthermore relate to a method that serves to control a movement of a mobile medical device, wherein the medical device includes a sensor unit having at least one sensor and a control apparatus, wherein the control apparatus specifies a movement path for the movement of the medical device on the basis of signals detected by the at least one sensor of the sensor unit. The medical device moves in particular along the movement path. Toward that end the control apparatus may control an, in particular, omnidirectional, chassis of the medical device.

One embodiment variant provides that the movement path is specified on the basis of lane markings and/or position markers detected by the at least one sensor. The sensors of the sensor unit may be embodied to detect lane markings for a specified movement direction of the medical device and/or a specified orientation of the medical device. The control unit may control the medical device on the basis of the position of the lane markings. The lane marking may in this case be embodied as continuous in the manner of a traffic lane for the medical device. Alternatively, the lane marking may also include individual discrete path markers. The path markers are, in this case, advantageously embodied so as to be identifiable for the control apparatus and have a position that is known to the control apparatus. The lane markings may also provide information about the desired orientation of the chassis of the medical device.

One embodiment variant provides that the medical device is moved from a start position to an end position, wherein, during the movement, pattern structures and/or position markers in an environment of the medical device are detected by the at least one sensor of the sensor unit. In this case, the movement path from the end position back to the start position is specified on the basis of the detected pattern structures and/or position markers. In this case, the pattern structures and/or position markers may be detected by an environmental sensor of the sensor unit. Pattern structures may be, for example, patterns on floor, ceiling, or walls. Position markers may be, for example, ceiling lights, ventilation openings, smoke alarms, or specially installed dedicated position markers that are located in the environment of the medical device. The control apparatus may record a progression of a relative change in the position of the medical device and/or a change in the orientation of the chassis of the medical device on the basis of the pattern structures and/or position markers detected by the environmental sensor. In this case, there is no need for the absolute positions of the pattern structures and/or of the position markers to be known. Deviations in the position of the medical device, (for example, on account of wheel slip or non-ideal geometry of the chassis of the medical device), may be automatically compensated by the control apparatus. Accordingly, the environmental sensor enables a movement of the medical device from a start position to an end position to be tracked, the medical device being able to perform, again automatically, a movement from the end position back to the start position.

One embodiment variant provides that the movement path is specified on the basis of spatial contours detected by the at least one sensor of the sensor unit. For this purpose, the control apparatus is advantageously embodied to detect the contours. Contours may in this case be, for example, walls on the basis of which the control apparatus controls the chassis of the medical device in such a way that the medical device moves, for example, at a predefined distance from the walls. In this case, the orientation of the chassis of the medical device may be adjusted automatically by the control apparatus to the progression of the contours. If the control apparatus detects a discontinuity in the contour, (for example, a corner in a corridor), the control apparatus may adjust the orientation of the chassis of the medical device to a new direction by a rotary movement about an axis of rotation. If a manual control action by the operator is superimposed on the automatic control of the movement of the medical device on the basis of the contours, the operator now has merely to adjust the speed of the medical device, since the direction of movement may be set automatically by the control apparatus on the basis of the detected contours.

One embodiment variant provides that the control apparatus includes at least one control element, an intervention in the movement of the medical device being effected by the control element. The intervention in the movement of the medical device is initiated, in particular, by an operator by the control element. In particular, the movement of the medical device may deviate from the movement path following the intervention. Accordingly, the operator may cause the medical device to avoid an obstacle, for example, or steer the medical device onto an alternative, in particular, adjacent, movement path. The intervention in the movement of the medical device may also correct a speed of movement of the medical device. Accordingly, the automatic control of the movement of the medical device on the movement path may advantageously be overlaid with a manual control of the movement of the medical device by the operator by the control element.

One embodiment variant provides that in the event of a deviation of the movement of the medical device from the movement path on account of the intervention in the movement of the medical device, the control apparatus will guide the medical device back onto the movement path. Accordingly, the movement path is embodied in particular as an ideal movement path for the medical device. The control apparatus may guide the medical device back onto the ideal movement path all the more forcibly, the further the chassis deviates from the ideal movement path. Accordingly, the user, for example, applies a greater force to the control element in order to cause the medical device to deviate further from the ideal movement path by manual control. The control apparatus may also specify a maximum deviation from the ideal movement path that may not be exceeded. The medical device may also have a switchover unit that enables an operator to toggle between manual control and automatic control of the movement of the medical device. Automatic guidance of the medical device back onto the movement path, in particular, in combination with the manual control of the movement of the medical device, allows a particularly simple, yet nonetheless manually adjustable, control of the movement of the medical device.

Features, advantages or alternative embodiments of the medical device may be transferred analogously to features, advantages or alternative embodiments of the method. Equally, features, advantages or alternative embodiments of the method may also be transferred to the medical device. In other words, the device-related claims may also be developed by the features that are described or claimed in connection with a method. The corresponding functional features of the method are in this case embodied by corresponding device-related modules, in particular by hardware modules.

DETAILED DESCRIPTION

Figure 1:
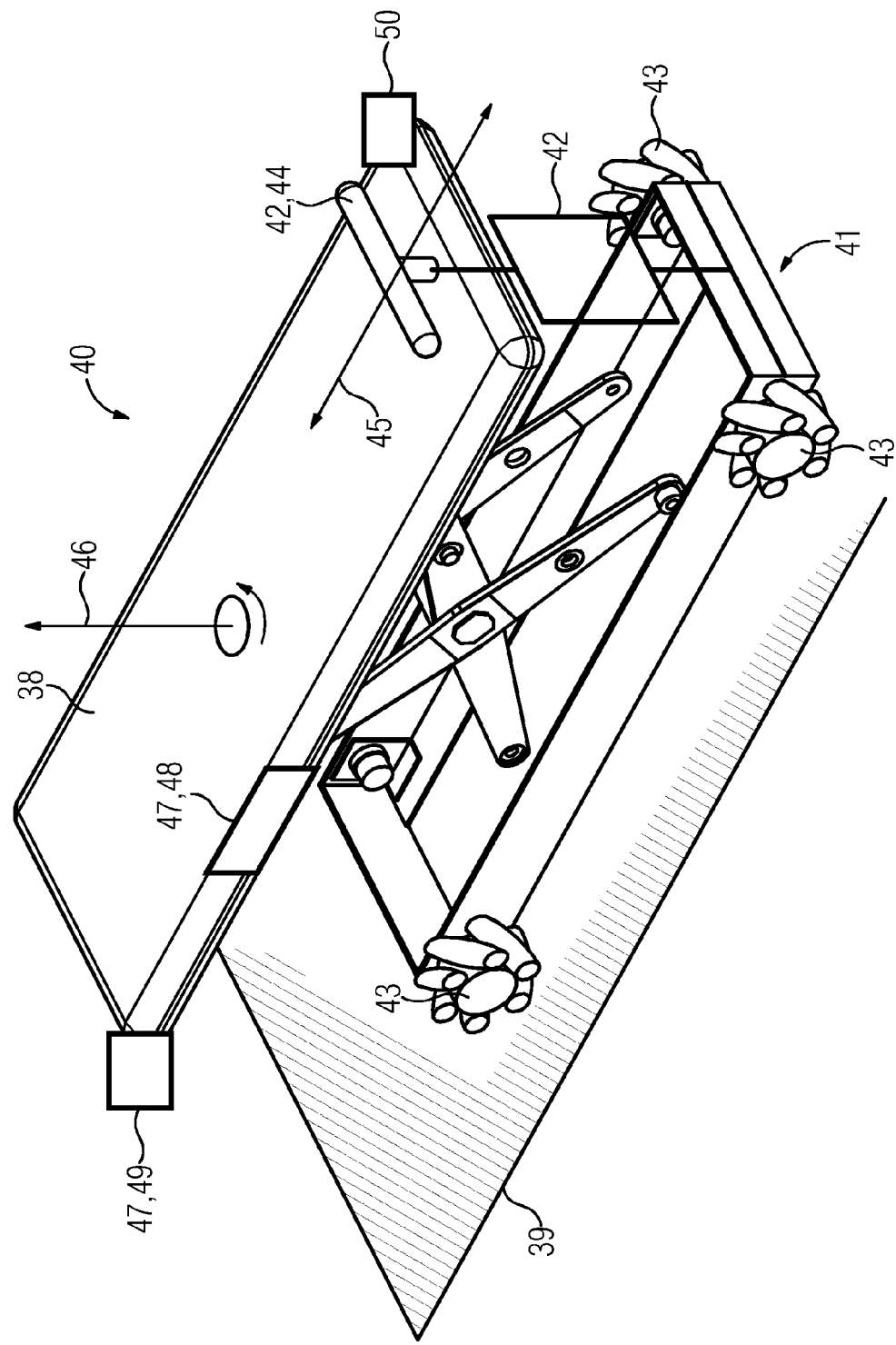
FIG. 1 depicts a schematic illustration of an embodiment of a medical device.

FIG. 1 depicts a medical device 40 in a schematic illustration. In the case depicted in FIG. 1, the medical device 40 is embodied as a mobile patient couch for a medical imaging device. For that purpose, the depicted medical device 40 has a support surface 38 for a patient (not depicted). The medical imaging device is, for example, a magnetic resonance device, a single-photon emission tomography device (SPECT device), a positron emission tomography device (PET device), a computed tomography device, an ultrasound device, an X-ray device, or an X-ray device embodied as a C-arm device. The medical device 40 may also be a mobile patient couch for a combined medical imaging apparatus including an arbitrary combination of a number of the cited imaging modalities.

Alternatively, the medical device 40 depicted in FIG. 1 may also be a mobile patient couch for an interventional examination apparatus and/or a treatment apparatus, (for example, an angiographic, cardiological, nephrological or urological examination apparatus and/or treatment apparatus). Alternatively, the illustrated medical device 40 may also be a mobile operating table and/or a mobile hospital bed.

Other mobile medical devices, which have no support surface for a patient, are also conceivable. Thus, the mobile medical device may also be a mobile gantry for a medical imaging device. Alternatively, the mobile medical device 40 may be a mobile X-ray system for radiography, fluoroscopy, or mammography. The mobile medical device 40 may also be embodied as a mobile C-arm X-ray system for a surgical, angiographic, or cardiological application. It is furthermore conceivable that the medical device 40 is a mobile diagnostic station and/or an operator control station for medical personnel. The medical device 40 may also be embodied as a mobile device for intensive medicine, for example, as a mobile monitoring device, respiratory device, infusion device, and/or dialysis device. Finally, the medical device 40 may also be a mobile robot system for medical applications.

The medical device 40 depicted in FIG. 1, (the mobile patient couch 40), includes a chassis 41 that, by way of example, includes roller elements, four omnidirectional wheels 43 in the case depicted. The patient couch 40 is embodied by the chassis 41 to perform an, (in particular, omnidirectional), movement in more than one spatial direction on a plane of motion 39 and to execute a rotary movement about an axis of rotation 46 standing perpendicularly on the plane of motion 39.

The patient couch 40 additionally includes a control apparatus 42. The control apparatus 42 is embodied for controlling the chassis 41. In this arrangement, the control apparatus 42 is coordinated with the chassis 41 in such a way that the control apparatus 42 is embodied to control the, in particular, omnidirectional, movement of the patient couch 40 on the plane of motion 39 and to control the rotary movement of the patient couch 40 about the axis of rotation 46.

For that purpose, the control apparatus 42 includes a control element 44 that is embodied for controlling the chassis 41 and is provided to be operated by an operator 45. In FIG. 1, the control element 44 is embodied simply as a handle. Furthermore, the operator 45 is not depicted explicitly. Only the movement of the control element 44 executed by the operator 45 in a spatial direction for the purpose of controlling the movement of the patient couch 40 is depicted. The control element 44 is in this case connected to the chassis 41, in particular, the omnidirectional wheels 43, by way of the control apparatus 42. The connection between the control element and the chassis 41 may in this case be embodied mechanically and/or electronically and/or with a view to an exchange of data.

The patient couch 40 additionally includes a sensor unit having a plurality of sensors 47. The control apparatus 42 is able to control the chassis 41 on the basis of signals detected by at least one sensor 47 of the sensor unit. This automatic control of the movement of the patient couch 40 may in this case be superimposed on the manual control of the movement of the patient couch 40 by the operator 45 by the control element 44. Among other components the patient couch 40 includes an environmental sensor 48 that is embodied to detect signals from a spatial environment of the patient couch 40. The patient couch 40 additionally includes an obstacle sensor 49 that is embodied to detect signals from obstacles in respect of the movement of the patient couch 40.

Possibilities for automatic control of the movement of the patient couch 40 by the signals detected by the sensors 47 are depicted in FIGS. 7-11.

Furthermore, the operator 45 is afforded the option of specifying a destination for the movement of the patient couch 40. For that purpose, the control apparatus 42 includes a destination specification unit 50 that allows an operator 45 to choose a destination for the patient couch 40, the control apparatus 42 moving the patient couch 40 to the chosen destination by the chassis 41.

Figure 2:
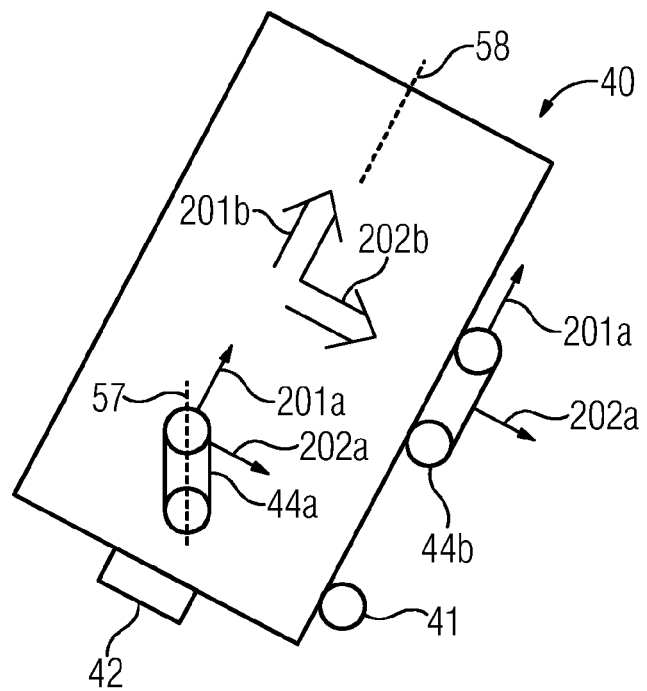
FIG. 2 depicts an embodiment of a manual control of a movement of a medical device by two control elements.
Figure 3:
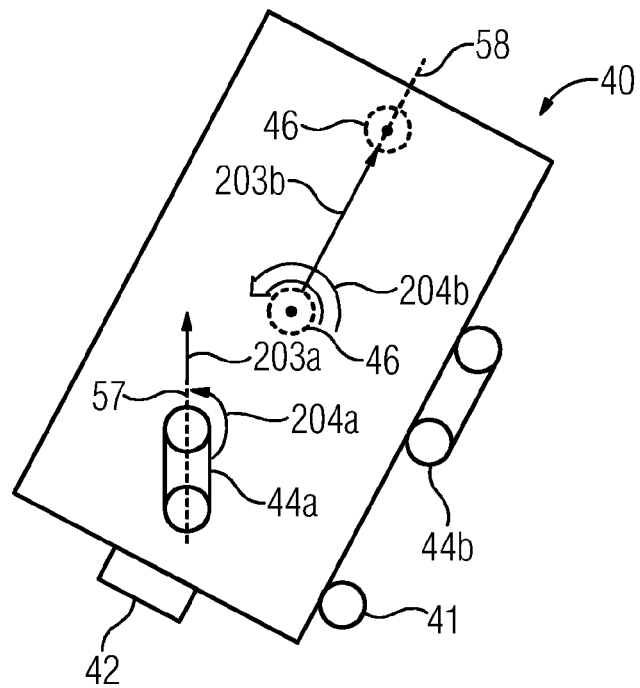
FIG. 3 depicts a further embodiment of a manual control of a movement of a medical device by a control element.

An alternative embodiment of the medical device 40 compared to FIG. 1 is depicted in FIG. 2 and FIG. 3. In particular, the medical device 40 is now no longer necessarily embodied as a patient couch 40. The following description restricts itself essentially to the differences compared to the exemplary embodiment in FIG. 1, with reference being made in respect of like components, features and functions to the description of the exemplary embodiment in FIG. 1. Components, features, and functions remaining essentially the same are numbered consistently with the same reference signs.

FIG. 2 depicts a manual control of a movement of a medical device 40 by two control elements 44a, 44b. Operating one control element 44a, 44b may be sufficient to move the medical device 40. The operator 45 is therefore free to use one of the control elements 44a, 44b in order to control the medical device 40. In the case depicted in FIG. 2, the medical device 40 includes a first control element 44a arranged at the head end of the medical device 40. The first control element 44a is embodied as a joystick. The medical device 40 includes a second control element 44b arranged at the side of the medical device 40. The second control element 44b is embodied by way of example as a guide bar.

Both control elements 44a, 44b may be moved by the operator 45 along a first control element movement direction 201a and a second control element movement direction 202a. In this case the first control element movement direction 201a is aligned along a longitudinal direction 58 of the medical device 40 and the second control element movement direction 202a is aligned perpendicularly to the first control element movement direction 201a and parallel to the plane of motion 39. Thus, the first control element movement direction 201a corresponds to a tilting of the first control element 44a along the longitudinal direction 58 of the medical device 40, in a forward direction by way of example in the case depicted in FIG. 2, and the second control element movement direction 202a corresponds to a tilting of the first control element 44a perpendicularly to the longitudinal direction 58 of the medical device 40 and parallel to the plane of motion 39, to the right in the case depicted in FIG. 2. In addition, the first control element movement direction 201a corresponds to a pulling of the second control element 44b along the longitudinal direction 58 of the medical device 40, and the second control element movement direction 202a to a pulling of the second control element 44b perpendicularly to the longitudinal direction 58 of the medical device 40 and parallel to the plane of motion 39.

The control elements 44a, 44b are connected to the chassis 41 of the medical device 40 via the control apparatus 42 in such a way that a movement of the control elements 44a, 44b along the first control element movement direction 201a triggers a movement of the medical device 40 by the chassis 41 along a first device movement direction 201b. The first control element movement direction 201a is in this case aligned parallel to the first device movement direction 201b. Thus, for example, a forward movement of the joystick leads to a forward movement of the medical device 40.

In addition, the control elements 44a, 44b are connected to the chassis 41 of the medical device 40 via the control apparatus 42 in such a way that a movement of the control elements 44a, 44b along the second control element movement direction 202a triggers a movement of the medical device 40 by the chassis 41 along a second device movement direction 202b. In this case the second control element movement direction 202a is also aligned parallel to the second device movement direction 202b.

In this case the movement of the control elements 44a, 44b may be transmitted to the movement of the chassis 41 of the medical device 40 mechanically and/or electronically by the control apparatus 42. The direction of movement of the control elements 44a, 44b may be, in this case, transferred electronically, with a view to an exchange of data, to the chassis 41. The actual movement of the medical device 40, in other words the motive force, is transmitted purely mechanically to the chassis 41.

FIG. 3 depicts a further manual control of a movement of the medical device 40 from FIG. 2 by the control elements 44a, 44b. The first control element 44a is represented in FIG. 3 as a joystick. The first control element 44a has a longitudinal axis 57. The first control element 44a is embodied to execute a control element rotary movement 204a about the longitudinal axis 57 of the first control element 44a, in particular, in addition to the control element movement in the first control element movement direction 201a and the second control element movement direction 202a. In this case, the control element rotary movement is likewise executed by the operator 45. In addition, the first control element 44a is embodied to execute a vertical movement 203a perpendicularly to the plane of motion 39. This provides, in the case depicted, that the first control element 44a may be pulled or pushed along its longitudinal axis 57 by the operator 45.

The first control element 44a is connected to the chassis 41 of the medical device 40 via the control apparatus 42 in such a way that the control element rotary movement 204a effects a rotary movement 204b of the medical device 40 by the chassis 41 about the axis of rotation 46. The direction of rotation of the individual roller elements, (e.g., in the clockwise or anticlockwise direction), of the rotary movement 204b of the medical device 40 in this case corresponds to the direction of rotation of the control element rotary movement 204a.

The first control element 44a is additionally connected to the chassis 41 of the medical device 40 via the control apparatus 42 in such a way that the vertical control element movement 203a of the first control element 44a perpendicularly to the plane of motion 39 initiates a displacement 203b of the axis of rotation 46 along the longitudinal direction 58 of the medical device 40. In the case depicted, for example, a vertical movement 203a of the first control element 44a upward, in the opposite direction to the force due to the weight of the medical device 40, leads to a displacement 203b of the axis of rotation 46 away from the operator 45 to the opposite foot end of the medical device 40. If the medical device 40 performs a rotary movement 204b following the displacement 203b of the axis of rotation 46, the rotary movement 204b is effected about the current displaced axis of rotation 46.

The movement of the first control element 44a may, in this case, once again be transmitted to the movement of the chassis 41 of the medical device 40 mechanically and/or electronically by the control apparatus 42. In this case, the direction of rotation of the first control element 44a may be transferred electronically, with a view to an exchange of data, to the chassis 41. The actual rotation of the medical device 40, (e.g., the torque), is transmitted purely mechanically to the chassis 41.

By a superposition of the linear movement of the control elements 44a, 44b depicted in FIG. 2 and the control element rotary movement 204a by the first control element 44a of FIG. 3 it is possible for the medical device 40 to negotiate corners with a variable radius.

Figure 4:
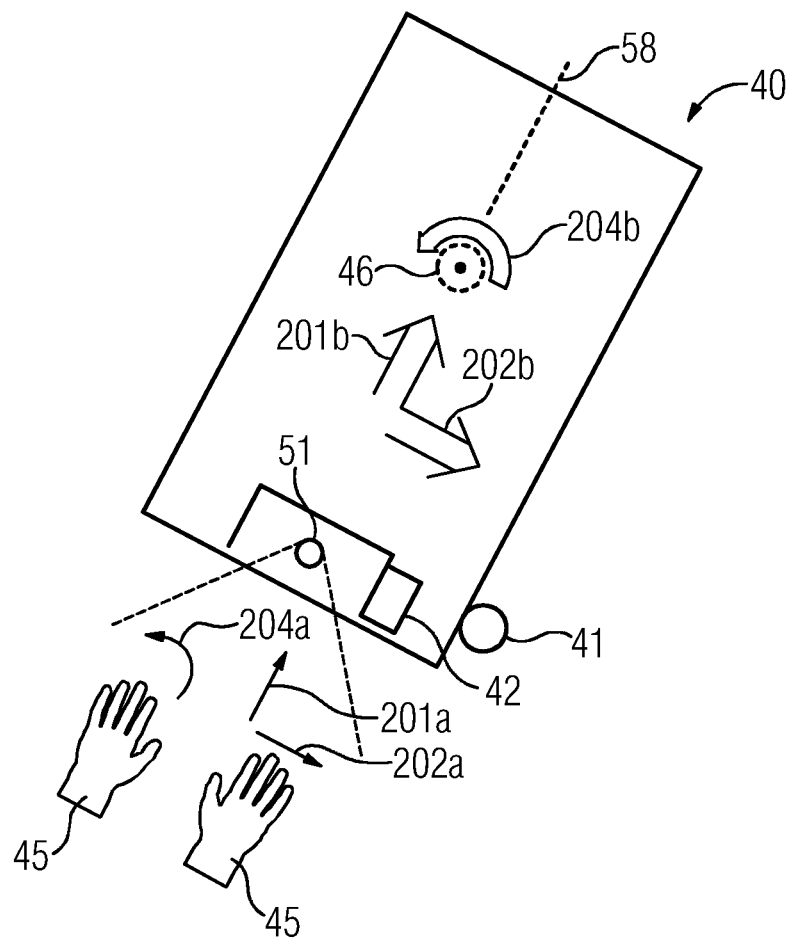
FIG. 4 depicts an embodiment of a manual control of a movement of a medical device by a contactless control element.

An alternative embodiment of the medical device 40 compared to FIGS. 1 to 3 is depicted in FIG. 4. The following description restricts itself essentially to the differences compared to the exemplary embodiment in FIGS. 1 to 3, with reference being made in respect of like components, features, and functions to the description of the exemplary embodiment in FIGS. 1 to 3. Components, features, and functions remaining essentially the same are numbered consistently with the same reference signs.

FIG. 4 depicts a manual control of a movement of a medical device 40 by a contactless control element 51. In the case depicted, the contactless control element 51 detects by an optical sensor, (e.g., a camera), gestures 201a, 202a, 204a made by the hands of the operator 45. The corresponding gestures 201a, 202a, 204a are in turn translated by the control apparatus 42 into equivalent movements 201b, 202b, 204b of the chassis 41 of the medical device 40.

Thus, a first gesture 201a along the longitudinal direction 58 of the medical device 40 leads to a forward movement of the medical device 40 along the first device movement direction 201b. A second gesture 202a to the right leads to a movement of the medical device 40 along the second device movement direction 202b perpendicularly to the longitudinal direction 58 of the medical device 40. A third gesture 204a, corresponding to a rotation of the hand of the operator 45, is translated into a rotary movement 204b of the medical device 40 about the axis of rotation 46.

Figure 5:
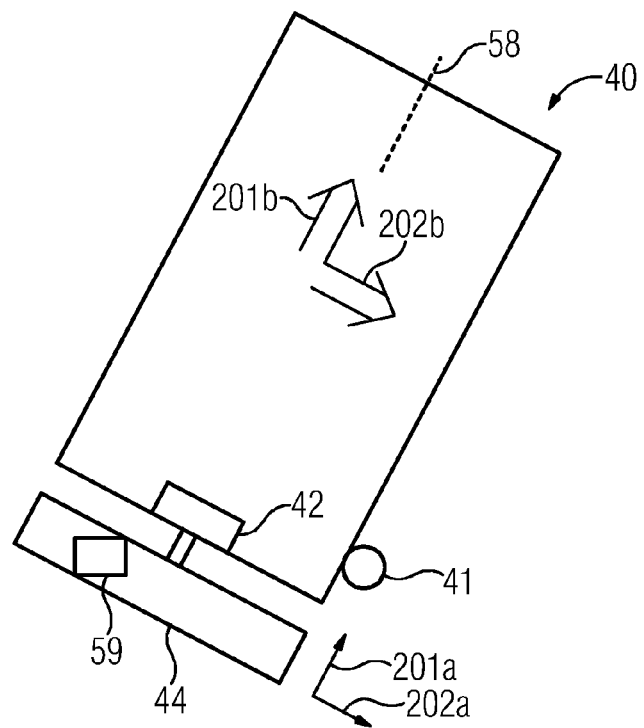
FIG. 5 depicts an embodiment of a manual control of a movement of a medical device by a control element having a force sensor.
Figure 6:
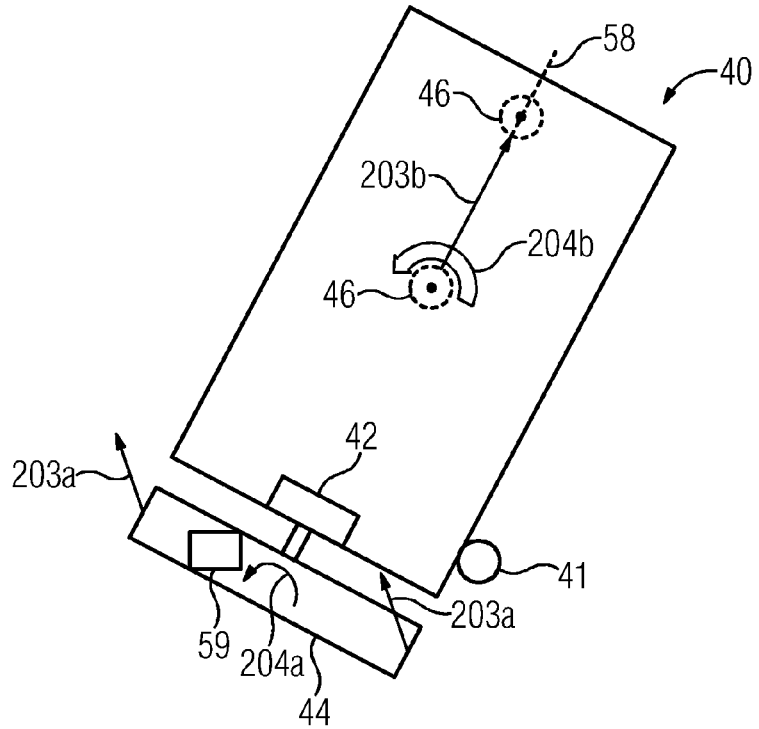
FIG. 6 depicts a further embodiment of a manual control of a movement of a medical device by a control element having a force sensor that is additionally configured as a torque sensor.

An alternative embodiment of the medical device 40 compared to FIGS. 1 to 4 is depicted in FIG. 5 and FIG. 6. The following description restricts itself essentially to the differences compared to the exemplary embodiment in FIGS. 1 to 4, with reference being made in respect of like components, features, and functions to the description of the exemplary embodiment in FIGS. 1 to 4. Components, features, and functions remaining essentially the same are numbered consistently with the same reference signs.

FIG. 5 depicts a manual control of a movement of a medical device 40 by a control element 44 having a force sensor 59. In this case, the control apparatus 42 controls the chassis 41 on the basis of a force acting on the control element 44 and measured by the force sensor 59. The force sensor 59 detects a direction of a force acting on the control element as well as a strength of the force acting on the control element.

In the case depicted, the control element 44 is embodied as a handlebar. The handlebar is connected to a force sensor 59, the force sensor 59 being integrated in the control apparatus 42. The control apparatus 42 detects the force exerted on the handlebar by the operator 45. On the basis of an equation of motion, in particular, including virtual mass and friction of the medical device 40 that is to be moved, the control apparatus 42 controls the chassis 41.

Once again, movements of the control element 44 along a first control element movement direction 201a and a second control element movement direction 202a are depicted by way of example. These in turn lead to a movement of the medical device 40 along the first device movement direction 201b or the second device movement direction 202b.

In this case, the magnitude and direction of the forces exerted on the control element 44 by the operator 45 are advantageously detected directly by the force sensor 59. The control apparatus 42 may control the direction and speed of movement of the medical device 40 on the basis of the magnitude and direction of the forces. A change in the magnitude of the force may trigger a change in the speed of movement of the medical device 40. A change in the force direction may trigger a change in the direction of movement of the medical device 40. For that purpose the medical device 40 includes a motor unit (not depicted) that generates a driving torque for the chassis 41.

In the case depicted, the handlebar is rigidly connected to the chassis 41 such that there is imparted to the operator 45 the intuitive control sensation that the operator 45 is executing the movement of the medical device 40 by his or her own force. Jerky movements of the handlebar by the operator 45 may be translated into jerk-free travel movements of the medical device 40.

FIG. 6 depicts a further manual control of a movement of the medical device 40 by the control element 44 having the force sensor 59. Once again, a control element rotary movement 204a and a vertical movement 203a of the control element 44 are depicted. These effect the corresponding rotary movement 204 of the medical device 40 about the axis of rotation 46 or the displacement 203b of the axis of rotation 46 (see FIG. 3).

A change in the strength of the control element rotary movement 204a may trigger a change in the speed of the rotary movement 204 of the medical device 40. A change in the direction of the control element rotary movement 204a may trigger a change in the direction of rotation of the medical device 40.

For this purpose, the force sensor 59 may advantageously also detect torques and accordingly be embodied in addition as a torque sensor. The torques may be detected by the control apparatus 42, in which case the control apparatus 42 may control the corresponding rotary movement 204b of the medical device 40.

An alternative embodiment of the medical device 40 compared to FIGS. 1 to 6 is depicted in FIGS. 7 to 11. The following description restricts itself essentially to the differences compared to the exemplary embodiment in FIGS. 1 to 6, with reference being made in respect of like components, features, and functions to the description of the exemplary embodiment in FIGS. 1 to 6. Components, features, and functions remaining essentially the same are numbered consistently with the same reference signs.

FIG. 7 to FIG. 11, in each case, depict a special implementation of an automatic control of a movement of a medical device 40. The medical device 40 is in principle embodied analogously to the description relating to FIGS. 1 to 6.

The medical device 40 has in each case a sensor unit having a plurality of sensors 47, of which one sensor 47 is depicted by way of example, and a control apparatus 42. On the basis of signals detected by the sensor 47 of the sensor unit, the control apparatus 42 specifies a movement path 52 for the movement of the medical device 40. The control apparatus 42 controls the chassis 41 of the medical device 40 in such a way that the medical device 40 moves on the specified movement path 52.

Figure 7:
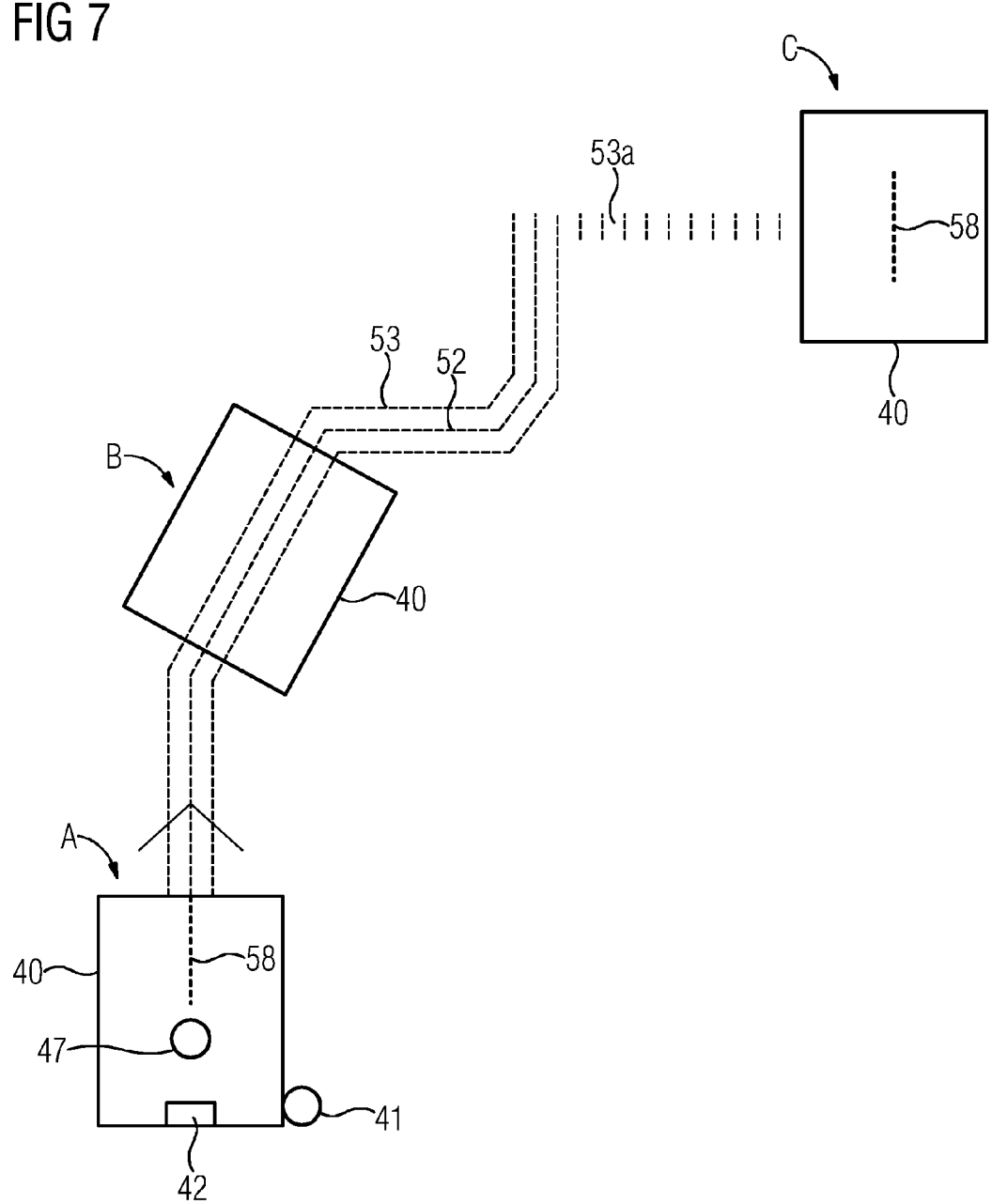
FIG. 7 depicts an embodiment of an automatic control of a movement of a medical device on the basis of a continuous lane marking.

FIG. 7 depicts an automatic control of a movement of the medical device 40 on the basis of a continuous lane marking 53.

In FIG. 7, the sensor 47 of the sensor unit is configured for lane detection for that purpose. A continuous lane marking 53 is detected, (e.g., sampled), by the sensor 47 and the movement path 52 is specified on the basis of the detected lane marking 53. Toward that end the sensor 47 relays a detected lane marking signal to the control apparatus 42. The control apparatus 42 controls the chassis 41 of the medical device 40 on the basis of the detected lane marking signals in such a way that the medical device 40 follows the lane marking 53 in its movement.

The lane marking 53 simultaneously encodes the orientation angle of the chassis 41 of the medical device 40 relative to the longitudinal direction 58 of the medical device 40. In the case depicted, the lane marking 53 includes strips, the direction of the strips indicating the orientation of the chassis 41 40. In the present case, the longitudinal direction 58 of the medical device 40 is aligned here over the greatest part of the route along the movement path 52 defined by the continuous lane marking 53. At the end of the movement path 52, the strips of the lane marking 53 change their orientation so that the medical device 40 follows an end section 53a of the lane marking with an orientation of the chassis 41 rotated through 90°. In this way, the medical device 40 reaches a parking position C, in an equipment depot, for example, in the correct alignment.

Thus, at position A and position B, the longitudinal direction 58 of the medical device 40 is aligned along the lane marking 53. At position C, the longitudinal direction 58 of the medical device 40 is aligned perpendicularly to the lane marking 53.

It is particularly advantageous in this situation that the chassis 41 of the medical device 40 is embodied as an omnidirectional chassis 41, for example, having omnidirectional wheels 43. This namely makes it particularly easy for the medical device 40 to follow changes in direction in the movement path 52 that are predefined by the lane marking 53.

Figure 8:
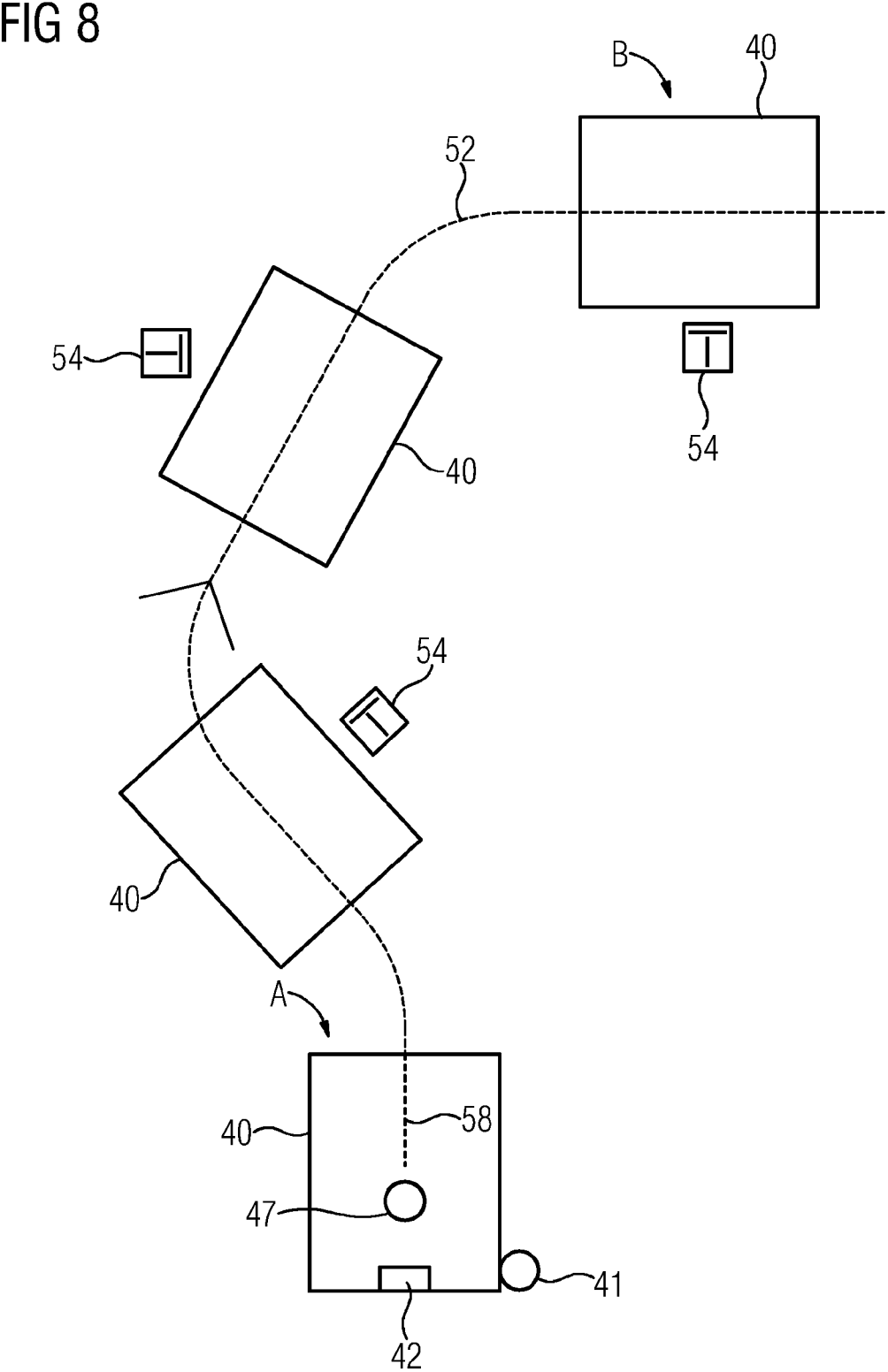
FIG. 8 depicts an embodiment of an automatic control of a movement of a medical device on the basis of position markers.

FIG. 8 depicts an automatic control of a movement of a medical device 40 on the basis of position markers 54.

In FIG. 8, the sensor 47 of the sensor unit is for that purpose configured to detect the position markers 54. The position markers are detected by the sensor 47 and the movement path 52 is specified on the basis of the detected position markers 54. For that purpose, the sensor 47 relays a detected position marker signal to the control apparatus 42. The control apparatus 42 controls the chassis 41 of the medical device 40 on the basis of the detected position marker signal in such a way that in its movement the medical device 40 follows the position markers 54 from a position A to a position B.

In this case, the movement path 52 has advantageously been preplanned or determined algorithmically. The movement path 52 is traveled automatically along the position markers 54. In this case, the position markers 54 also provide information about the orientation of the chassis 41.

The absolute positions of the position markers 54 and the orientation of the position markers 54 are in this case stored in a memory unit of the control apparatus 42. Accordingly, the control apparatus 42 may determine the current location and orientation of the medical device 40 at any time by a referencing to a position marker 54 and accordingly guide the medical device 40 along the specified movement path 52.

Figure 9:
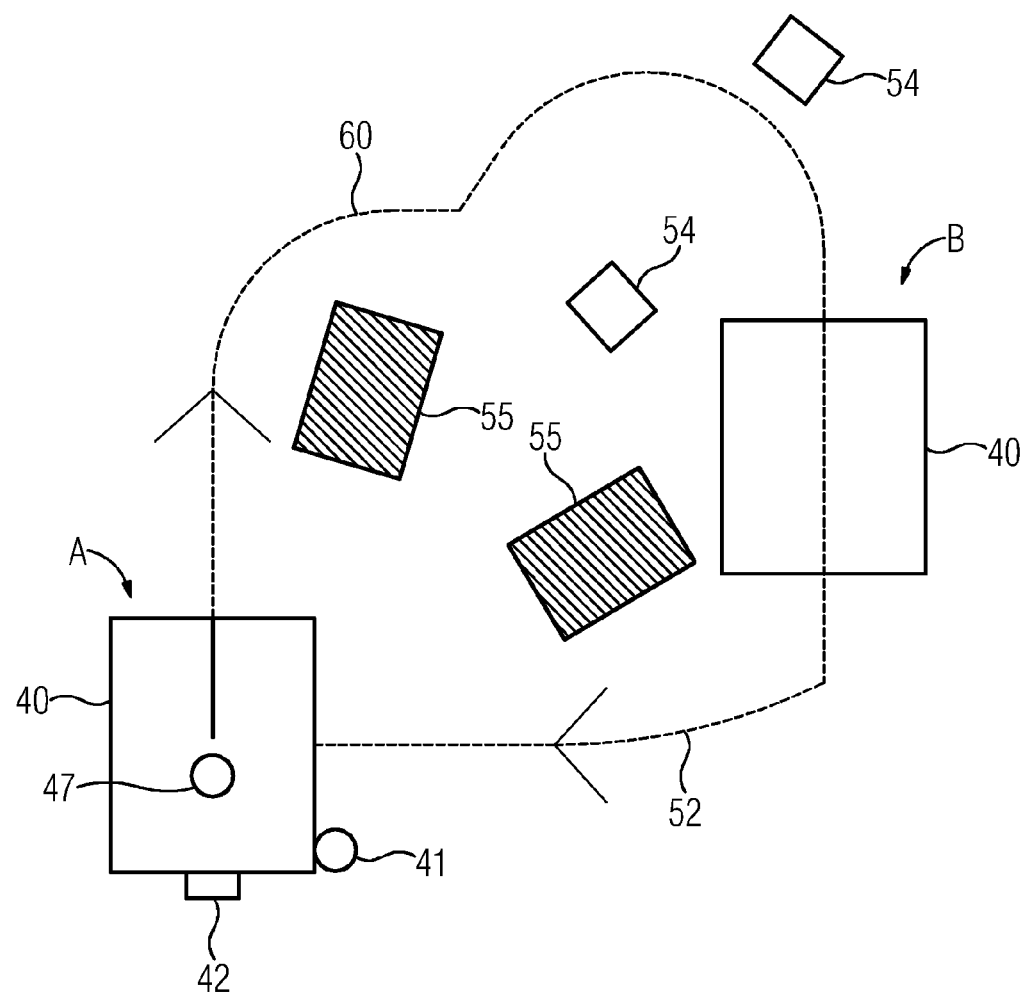
FIG. 9 depicts an embodiment of an automatic control of a movement of a medical device from an end position back to a start position.

FIG. 9 depicts an automatic control of a movement of a medical device 40 from an end position B back to a start position A.

In the case depicted, the start position A is, by way of example, a parking position of the medical device 40, in an equipment depot, for example. In the case depicted, the end position B is, by way of example, a deployment site of the medical device 40. Accordingly, following completion of its deployment at the end position B, the medical device 40 is to be moved back again automatically to the start position A.

Conversely, the case may of course also apply whereby the start position A is the deployment site and the end position B is the parking position. An example of this case is the deployment of a medical device 40 embodied as a mobile C-arm X-ray system in an operating room: At the deployment site of the medical device 40, the start position A, a first X-ray image is acquired of a patient positioned on an operating table. The medical device 40 is thereafter driven under manual or automatic control to a park position, the end position B. In this way, the medical device 40 does not impede the work being carried out at the operating table. Later, the medical device 40 may automatically return to the previous deployment site and in turn acquire a second X-ray image. The image sections of the first and second X-rays will coincide.

During the movement of the medical device 40 from the start position A to the end position B, the outward leg 60, the sensor 47 in this case detects pattern structures 55 and position markers 54 in an environment of the medical device 40. On the outward leg 60, the movement of the medical device 40 is controlled manually by the operator 45. The movement path 52 from the end position B back to the start position A is specified by the control apparatus 42 on the basis of the detected pattern structures 55 and position markers 54. In this case, the sensor 47 again detects the pattern structures 55 and position markers 54 on the movement path 52.

The absolute position of the pattern structures 55 and position markers 54 does not need to be known in this case. Accordingly, the control apparatus 42 may specify the movement path 52 of the medical device 40 also on the basis of pattern structures 55 and position markers 54 occurring randomly in the environment of the medical device 40. Random pattern structures 55 may in this context be, for example, patterns on floor, ceiling, or walls. Random position markers 54 may in this context be, for example, ceiling lights, ventilation openings, or smoke alarms. Specifically installed dedicated pattern structures 55 and position markers 54 may of course also be used for determining the movement path 52.

In the case depicted in FIG. 9, the movement path 52 back is different from the path on the outward leg 60. For this purpose, topographical information about the environment of the medical device 40, (e.g., a plan of the hospital), is stored on a memory unit of the control apparatus 42. Alternatively, the movement path 52 back may also be identical to the path on the outward leg 60.

Figure 10:
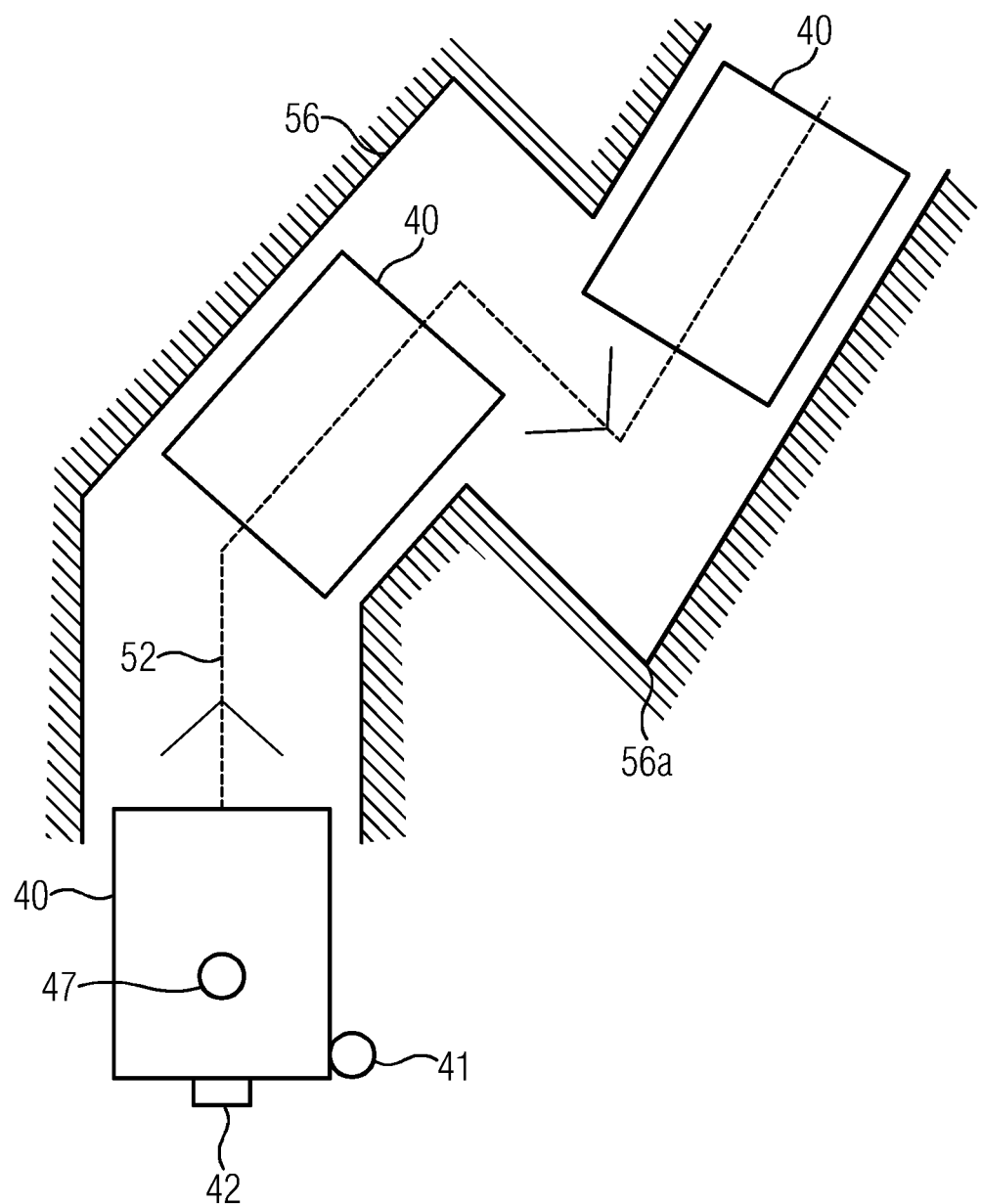
FIG. 10 depicts an embodiment of an automatic control of a movement of a medical device on the basis of spatial contours.

FIG. 10 depicts an automatic control of a movement of a medical device 40 on the basis of spatial contours 56.

In FIG. 10, the sensor 47 of the sensor unit is to that end configured to detect the spatial contours 56, for example, as an environmental sensor 48. The spatial contours 56 are detected, (e.g., sampled), by the sensor 47, and the movement path 52 is specified on the basis of the detected spatial contours 56. For that purpose, the sensor 47 relays a detected contour signal to the control apparatus 42. The control apparatus 42 controls the chassis 41 of the medical device 40 on the basis of the detected contour signal in such a way that the medical device 40 adjusts its movement to suit the spatial contours 56.

In the case depicted, the spatial contours 56 are the walls, of a corridor for example, which are located in the environment of the medical device 40. The movement path 52 is specified by the control apparatus 42 in such a way that the medical device 40 moves at a predefined distance, (in particular, a minimum distance), from the walls. The orientation of the chassis 41 is automatically adjusted to the progression of the spatial contours 56. The speed of movement of the medical device 40 may in this case be specified manually by the operator 45 or automatically.

In the case depicted, a discontinuity 56a in the spatial contours 56 is present. The discontinuity 56a is embodied as a corner in the walls. The orientation of the chassis 41 is adjusted at the discontinuity 56a of the spatial contours 56 such that the movement of the medical device 40 is oriented at a desired distance from the walls. Here too, the use of the omnidirectional chassis 41 is once again advantageous.

Figure 11:
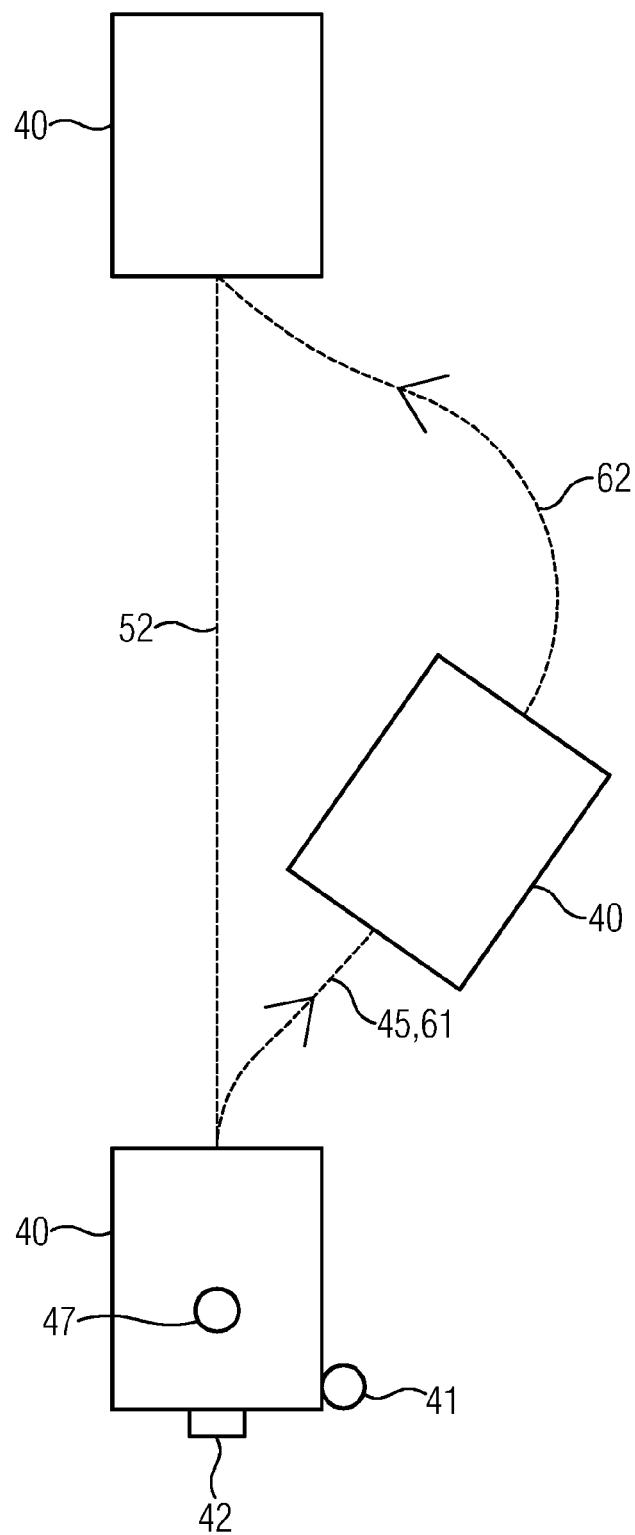
FIG. 11 depicts an embodiment of an automatic guidance of a medical device back onto a movement path following a deviation of the medical device from the movement path.

FIG. 11 depicts an automatic guidance of a medical device 40 back onto a movement path 52 following a deviation of the medical device 40 from the movement path 52. For this purpose, the control apparatus 42 includes at least one control element 44 that enables an operator 45 to intervene in the movement of the medical device 40.

In this case, the sensor 47 may send the control apparatus 42 a signal by which the control apparatus 42 recognizes that the medical device 40 has deviated from the movement path 52. In the case depicted in FIG. 11, the movement path is predefined and known to the control apparatus 42.

The deviation of the medical device 40 from the movement path 52 leads the medical device 40 onto a diverging movement path 61 and in the case depicted is initiated as a result of the manual intervention by the operator 45, in particular, by a control element (not depicted), so that the medical device 40 may avoid an obstacle, for example. Once the intervention on the part of the operator 45 has been terminated, the control apparatus 42 automatically guides the medical device 40, following a return path 62, from the diverging movement path 61 back onto the movement path 52.

It is self-evident that any combination whatsoever of the sensors 47 and possibilities for automatic control of the medical device 40 illustrated in FIGS. 7-11 may be used.

Although the invention has been illustrated and described in greater detail on the basis of the exemplary embodiments, the invention is nonetheless not limited by the disclosed examples, and other variations may be derived herefrom by the person skilled in the art without leaving the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical device comprising:
a chassis; and
a controller,
wherein the medical device is configured by the chassis to move in at least two spatial directions on a plane of motion and to rotate about an axis of rotation perpendicular to the plane of motion, and
wherein the controller comprises at least one control element configured to control the chassis,
wherein the at least one control element is configured to be manually operated by an operator,
wherein the at least one control element comprises a longitudinal axis and is configured to perform a control element rotary movement about the longitudinal axis of the at least one control element, and
wherein the controller is configured to initiate a rotary movement of the medical device about the axis of rotation based on the control element rotary movement.

2. The medical device as claimed in claim 1, wherein the chassis comprises at least omnidirectional wheels.

3. A medical device comprising:
a chassis; and
a controller,
wherein the medical device is configured by the chassis to move in at least two spatial directions on a plane of motion and to rotate about an axis of rotation perpendicular to the plane of motion, and
wherein the controller comprises at least one control element configured to control the chassis,
wherein the at least one control element is configured to be manually operated by an operator,
wherein the at least one control element is configured to perform a vertical control element movement perpendicularly to the plane of motion, and
wherein the controller is configured to initiate a displacement of the axis of rotation of the medical device based on the vertical control element movement of the at least one control element.

4. The medical device as claimed in claim 1, wherein the at least one control element is configured to perform a vertical control element movement perpendicularly to the plane of motion, and
wherein the controller is configured to initiate a displacement of the axis of rotation of the medical device based on the vertical control element movement of the at least one control element.

5. The medical device as claimed in claim 1, wherein the at least one control element comprises a force sensor, and
wherein the controller controls the chassis based on a force acting on the at least one control element and measured by the force sensor.

6. The medical device as claimed in claim 1, wherein the medical device comprises a sensor unit having at least one sensor, and
wherein the controller controls the chassis based on signals detected by the at least one sensor of the sensor unit.

7. The medical device as claimed in claim 6, wherein the sensor unit comprises at least one environmental sensor configured to detect signals from a spatial environment of the medical device.

8. The medical device as claimed in claim 6, wherein the sensor unit comprises at least one obstacle sensor configured to detect signals from obstacles in respect of the movement of the medical device.

9. The medical device as claimed in claim 1, wherein the controller comprises a destination specification unit that enables an operator to choose a destination for the medical device, and
wherein the controller moves the medical device by the chassis to the chosen destination.

10. A method for controlling a movement of a mobile medical device comprising a sensor unit having at least one sensor and a controller, the method comprising:
moving the medical device from a start position to an end position;
detecting, during the movement, pattern structures, position markers, or pattern structures and position markers in an environment of the medical device by the at least one sensor of the sensor unit;
specifying, by the controller, a movement path for the movement of the medical device based on the detected pattern structures, position markers, or pattern structures and position markers; and
moving the medical device from the end position back to the start position along the movement path.

11. The method as claimed in claim 10, wherein the movement path is specified based on spatial contours detected by the at least one sensor of the sensor unit.

12. The method as claimed in claim 10, wherein the controller comprises at least one control element, and
wherein an intervention in the movement of the medical device is effected by the control element.

13. The method as claimed in claim 12, wherein, following a deviation of the movement of the medical device from the movement path due to the intervention in the movement of the medical device, the controller guides the medical device back onto the movement path.

14. The medical device as claimed in claim 1, wherein the control element comprises a joystick, control lever, handlebar, or guide bar.

15. The medical device as claimed in claim 3, wherein the control element comprises a joystick, control lever, handlebar, or guide bar.

* * * * *